United States Patent [19]

Mondin et al.

[11] Patent Number: 5,759,983

[45] Date of Patent: *Jun. 2, 1998

[54] AQUEOUS CLEANING COMPOSITION WHICH MAY BE IN MICROEMULSION FORM COMPRISING POLYALKYLENE OXIDE -POLYDIMETHYL SILOXANE AND ETHOXYLATED SECONDARY ALCOHOL

[75] Inventors: Myriam Mondin, Seraing; Nicole Andries, Voroux-Lex-Liers; Jean Massaux, Olne, all of Belgium

[73] Assignee: Colgate-Palmolive Co., Piscataway, N.J.

[*] Notice: The term of this patent shall not extend beyond the expiration date of Pat. No. 5,741,760.

[21] Appl. No.: 698,604

[22] Filed: Aug. 16, 1996

Related U.S. Application Data

[63] Continuation-in-part of Ser. No. 336,936, Nov. 15, 1994, Pat. No. 5,549,840, which is a continuation-in-part of Ser. No. 192,118, Feb. 3, 1994, abandoned, which is a continuation-in-part of Ser. No. 155,317, Nov. 22, 1993, abandoned, which is a continuation-in-part of Ser. No. 102,314, Aug. 4, 1993, abandoned.

[51] Int. Cl.$^6$ .................. C11D 3/37; C11D 3/60; C11D 17/00

[52] U.S. Cl. .............. 510/365; 510/101; 510/238; 510/417; 510/422; 510/424; 510/425; 510/437; 510/466; 510/475; 510/505; 510/506; 510/508

[58] Field of Search ............ 510/365, 417, 510/421, 422, 424, 466, 475, 505, 506, 238, 101, 425, 437, 508

[56] References Cited

U.S. PATENT DOCUMENTS

| | | | |
|---|---|---|---|
| 3,294,726 | 12/1966 | Wyner | 260/29.6 |
| 3,580,853 | 5/1971 | Parran et al. | 252/152 |
| 3,839,234 | 10/1974 | Roscoe | 252/544 |
| 4,199,464 | 4/1980 | Cambre | 252/91 |
| 4,353,745 | 10/1982 | Ebbeler | 106/2 |
| 4,501,680 | 2/1985 | Aszman | 252/142 |
| 4,589,988 | 5/1986 | Rieck et al. | 252/8.8 |
| 4,690,779 | 9/1987 | Baker et al. | 252/546 |
| 5,008,030 | 4/1991 | Cook et al. | 252/106 |
| 5,075,026 | 12/1991 | Loth et al. | 510/101 |
| 5,076,954 | 12/1991 | Loth et al. | 134/40 |
| 5,082,584 | 1/1992 | Loth et al. | 510/101 |
| 5,108,643 | 4/1992 | Loth et al. | 510/238 |
| 5,164,120 | 11/1992 | Borland et al. | 252/546 |
| 5,167,872 | 12/1992 | Pancheri | 252/544 |
| 5,223,179 | 6/1993 | Connor et al. | 252/548 |
| 5,393,468 | 2/1995 | Erilli et al. | 252/550 |
| 5,403,509 | 4/1995 | Pujol et al. | 510/535 |
| 5,415,813 | 5/1995 | Misselyn et al. | 252/547 |
| 5,425,891 | 6/1995 | Pujol et al. | 510/355 |
| 5,496,492 | 3/1996 | Hamada et al. | 510/159 |
| 5,549,840 | 8/1996 | Mondin et al. | 510/365 |
| 5,558,806 | 9/1996 | Pollicello et al. | 252/355 |

FOREIGN PATENT DOCUMENTS

| | | |
|---|---|---|
| 0 579 887 | 1/1994 | European Pat. Off. |
| 0 586 323 | 3/1994 | European Pat. Off. |
| 57-209999 | 12/1982 | Japan . |
| 58-206693 | 12/1983 | Japan . |
| 1453385 | 10/1976 | United Kingdom . |

OTHER PUBLICATIONS

Chemical Abstracts Registry file computer printout for registry no. 183259–65–6, 1997.

*Primary Examiner*—Ardith Hertzog
*Attorney, Agent, or Firm*—Richard E. Nanfeldt; James M. Serafino

[57] ABSTRACT

An improvement is described in all purpose liquid cleaning composition and microemulsion composition which are especially effective in the removal of oily and greasy soil and contains a quick drying agent, an anionic detergent, optionally, a partially esterified ethoxylated polyhydric type alcohol, a secondary alcohol cosurfactant, a hydrocarbon ingredient, and water.

11 Claims, 2 Drawing Sheets

AMBIENT CONDITIONS:
TEMP: 23.4°C
HUMIDITY: 50.3%

FORMULA C ──▲──
FORMULA B ──□──
FORMULA A ──●──

AQUEOUS CLEANING COMPOSITION WHICH MAY BE IN MICROEMULSION FORM COMPRISING POLYALKYLENE OXIDE -POLYDIMETHYL SILOXANE AND ETHOXYLATED SECONDARY ALCOHOL

RELATED APPLICATION

This application is a continuation-in-part application of U.S. Ser. No. 8/336,936 filed Nov. 15, 1994 now U.S. Pat. No. 5,549,846 which in turn is a continuation-in-part application of U.S. Serial No. 8/192,118 filed Feb. 3, 1994 now abandoned which in turn is a continuation-in-part application of U.S. Serial No. 8/155,317 filed Nov. 22, 1993 now abandoned which is a continuation-in-part application of U.S. Serial No. 8/102,314 filed Aug. 4, 1993 now abandoned.

FIELD OF THE INVENTION

The present invention relates to a quick drying surface liquid cleaning composition comprising an ethoxylated glycerol type compound (as defined below) and/or a sulfonate surfactant and a block copolymer of a polyalkylene oxide-modified polydimethyl siloxane and a secondary alcohol of the formula $H(C_2H_4O)_xC_yH_{2y+2}O$, wherein x is 5 to 9 and y is 7 to 11.

BACKGROUND OF THE INVENTION

This invention relates to an improved all-purpose liquid cleaning composition or a microemulsion composition designed in particular for cleaning hard surfaces and which is effective in removing grease soil and/or bath soil and in leaving unrinsed surfaces with a shiny appearance.

In recent years all-purpose liquid detergents have become widely accepted for cleaning hard surfaces, e.g., painted woodwork and panels, tiled walls, wash bowls, bathtubs, linoleum or tile floors, washable wall paper, etc. Such all-purpose liquids comprise clear and opaque aqueous mixtures of water-soluble synthetic organic detergents and water-soluble detergent builder salts. In order to achieve comparable cleaning efficiency with granular or powdered all-purpose cleaning compositions, use of water-soluble inorganic phosphate builder salts was favored in the prior art all-purpose liquids. For example, such early phosphate-containing compositions are described in U.S. Pat. Nos. 2,560,839; 3,234,138; 3,350,319; and British Patent No.1, 223,739.

In view of the environmentalist's efforts to reduce phosphate levels in ground water, improved all-purpose liquids containing reduced concentrations of inorganic phosphate builder salts or non-phosphate builder salts have appeared. A particularly useful self-opacified liquid of the latter type is described in U.S. Pat. No. 4,244,840.

However, these prior art all-purpose liquid detergents containing detergent builder salts or other equivalent tend to leave films, spots or streaks on cleaned unrinsed surfaces, particularly shiny surfaces. Thus, such liquids require thorough rinsing of the cleaned surfaces which is a time-consuming chore for the user.

In order to overcome the foregoing disadvantage of the prior art all-purpose liquid, U.S. Pat. No. 4,017,409 teaches that a mixture of paraffin sulfonate and a reduced concentration of inorganic phosphate builder salt should be employed. However, such compositions are not completely acceptable from an environmental point of view based upon the phosphate content. On the other hand, another alternative to achieving phosphate-free all-purpose liquids has been to use a major proportion of a mixture of anionic and nonionic detergents with minor amounts of glycol ether solvent and organic amine as shown in U.S. Pat. No. 3,935,130. Again, this approach has not been completely satisfactory and the high levels of organic detergents necessary to achieve cleaning cause foaming which, in turn, leads to the need for thorough rinsing which has been found to be undesirable to today's consumers.

Another approach to formulating hard surfaced or all-purpose liquid detergent composition where product homogeneity and clarity are important considerations involves the formation of oil-in-water (o/w) microemulsions which contain one or more surface-active detergent compounds, a water-immiscible solvent (typically a hydrocarbon solvent), water and a "cosurfactant" compound which provides product stability. By definition, an o/w microemulsion is a spontaneously forming colloidal dispersion of "oil" phase particles having a particle size in the range of 25 to 800 Å in a continuous aqueous phase.

In view of the extremely fine particle size of the dispersed oil phase particles, microemulsions are transparent to light and are clear and usually highly stable against phase separation.

Patent disclosures relating to use of grease-removal solvents in o/w microemulsions include, for example, European Patent Applications EP 0137615 and EP 0137616 —Herbots et al; European Patent Application EP 0160762 —Johnston et al; and U.S. Pat. No. 4,561,991 —Herbots et al. Each of these patent disclosures also teaches using at least 5% by weight of grease-removal solvent.

It also is known from British Patent Application GB 21 44763A to Herbots et al, published Mar. 13, 1985, that magnesium salts enhance grease-removal performance of organic grease-removal solvents, such as the terpenes, in o/w microemulsion liquid detergent compositions. The compositions of this invention described by Herbots et al, require at least 5% of the mixture of grease-removal solvent and magnesium salt and preferably at least 5% of solvent (which may be a mixture of water-immiscible non-polar solvent with a sparingly soluble slightly polar solvent) and at least 0.1% magnesium salt.

However, since the amount of water immiscible and sparingly soluble components which can be present in an o/w microemulsion, with low total active ingredients without impairing the stability of the microemulsion is rather limited (for example, up to 18% by weight of the aqueous phase), the presence of such high quantities of grease-removal solvent tend to reduce the total amount of greasy or oily soils which can be taken up by and into the microemulsion without causing phase separation.

The following representative prior art patents also relate to liquid detergent cleaning compositions in the form of o/w microemulsions: U.S. Pat. No. 4,472,291—Rosario; U.S. Pat. No. 4,540,448 —Gauteer et al; U.S. Pat. No. 3,723, 330—Sheflin; etc.

Liquid detergent compositions which include terpenes, such as d-limonene, or other grease-removal solvent, although not disclosed to be in the form of o/w microemulsions, are the subject matter of the following representative patent documents: European Patent Application 0080749; British Patent Specification 1,603,047; and U.S. Pat. Nos. 4,414,128 and 4,540,505. For example, U.S. Pat. No. 4,414,128 broadly discloses an aqueous liquid detergent composition characterized by, by weight:

(a) from 1% to 20% of a synthetic anionic, nonionic, amphoteric or zwitterionic surfactant or mixture thereof;

(b) from 0.5% to 10% of a mono- or sesquiterpene or mixture thereof, at a weight ratio of (a):(b) being in the range of 5:1 to 1:3; and (c) from 0.5% 10% of a polar solvent having a solubility in water at 15° C. in the range of from 0.2% to 10%. Other ingredients present in the formulations disclosed in this patent include from 0.05% to 2% by weight of an alkali metal, ammonium or alkanolammonium soap of a $C_{13}$–$C_{24}$ fatty acid; a calcium sequestrant from 0.5% to 13% by weight; non-aqueous solvent, e.g., alcohols and glycol ethers, up to 10% by weight; and hydrotropes, e.g., urea, ethanolamines, salts of lower alkylaryl sulfonates, up to 10% by weight. All of the formulations shown in the Examples of this patent include relatively large amounts of detergent builder salts which are detrimental to surface shine.

Furthermore, the present inventors have observed that in formulations containing grease-removal assisting magnesium compounds, the addition of minor amounts of builder salts, such as alkali metal polyphosphates, alkali metal carbonates, nitrilotriacetic acid salts, and so on, tends to make it more difficult to form stable microemulsion systems.

U.S. Pat. No. 5,082,584 discloses a microemulsion composition having an anionic surfactant, a cosurfactant, nonionic surfactant, perfume and water; however, these compositions do not possess the ecotoxicity and the improved interfacial tension properties as exhibited by the compositions of the instant invention.

A number of patents teach esterified ethoxylated glycerol compounds for various applications. These patents are Great Britain 1,453,385; Japan 59-1600 and Japan 58-206693 and European Patent Application 0586,323A1. These publications fail to appreciate that a mixture of esterified ethoxylated glycerol and nonesterified ethoxylated glycerol, when used in a hard surface cleaning composition, functions as a grease release agent.

SUMMARY OF THE INVENTION

The present invention provides an improved, quick drying surface, liquid cleaning composition having improved interfacial tension which improves cleaning hard surface in the form of a microemulsion which is suitable for cleaning hard surfaces such as plastic, vitreous and metal surfaces having a shiny finish, oil stained floors, automotive engines and other engines. More particularly, the improved cleaning compositions exhibit improved drying times and good grease soil removal properties due to the improved interfacial tensions, when used in undiluted (neat) form and leave the cleaned surfaces shiny without the need of or requiring only minimal additional rinsing or wiping. The latter characteristic is evidenced by little or no visible residues on the unrinsed cleaned surfaces and, accordingly, overcomes one of the disadvantages of prior art products.

Surprisingly, these desirable results are accomplished even in the absence of polyphosphate or other inorganic or organic detergent builder salts and also in the complete absence or substantially complete absence of grease-removal solvent.

The instant compositions are more friendly for the environment due to the low ecotoxicity of ethoxylated polyhydric alcohol type compound (as defined below) such as an ethoxylated glycerol type compound used in the instant compositions.

The compositions of the instant invention have an ecotoxocity value as measured by the LC 50 test as deferred by The Organization for Economic Cooperation and Development (OECD)(of which the United States is a member) in OECD Test No. 202 of at least 0.18 ml/L measured on Daphniae microorganisms.

In one aspect, the invention generally provides a stable, optically clear microemulsion, hard surface cleaning composition especially effective in the removal of oily and greasy oil, which is in the form of a substantially dilute oil-in-water microemulsion having an aqueous phase and an oil phase; The dilute microemulsion composition includes, on a weight basis:

0.1% to 20% of an anionic surfactant;

0.1% to 10% of a block copolymer of a polyalkylene oxide-modified polydimethyl siloxane;

0.1% to 15% of a secondary alcohol of the formula $H(C_2H_4O)_xC_yH_{2y+2}O$ wherein x is 5 to 9 and y is 7 to 11;

0.1% to 10% of a compound which is a mixture of a partially esterified ethoxylated polyhydric alcohol, a fully esterified ethoxylated polyhydric alcohol and a nonesterified ethoxylated polyhydric alcohol (said mixture being herein after referred to as an ethoxylated polyhydric alcohol type compound such as an ethoxylated glycerol type compound);

0 to 15% of magnesium sulfate heptahydrate;

0.4 to 10.0% of a perfume, essential oil, or water insoluble hydrocarbon having 6 to 18 carbon atoms; and the balance being water.

Quite surprisingly although the perfume is not, per se, a solvent for greasy or oily soil,—even though some perfumes may, in fact, contain as much as 80% of terpenes which are known as good grease solvents—the inventive compositions in dilute form have the capacity to solubilize up to 10 times or more of the weight of the perfume of oily and greasy soil, which is removed or loosened from the hard surface by virtue of the action of the anionic and nonionic surfactants, said soil being taken up into the oil phase of the o/w microemulsion.

In a second aspect, the invention comprises an all purpose hard surface cleaning composition comprising approximately by weight:

0.1 % to 20% of an anionic surfactant;

0.1% to 10% of a block copolymer of a polyalkylene oxide-modified polydimethyl siloxane;

0.1% to 15%, more preferably 0.5% to 12% of a secondary alcohol of the formula $H(C_2H_4O)_xC_yH_{2y+2}O$ wherein x is 5 to 9 and y is 7 to 11;

0 to 10%, more preferably 0.1% to 10% of a perfume, essential oil or water insoluble hydrocarbon having 6 to 18 carbon atoms; and the balance being water.

In a third aspect, the invention generally provides highly concentrated microemulsion compositions in the form of either an oil-in-water (o/w) microemulsion or a water-in-oil (w/o) microemulsion which when diluted with additional water before use can form dilute o/w microemulsion compositions. Broadly, the concentrated microemulsion compositions contain, by weight, 0.1% to 30% of an anionic surfactant, 0.1% to 10% of said ethoxylated polyhydric alcohol type compound, 0.4% to 10% of perfume, essential oil or water insoluble hydrocarbon having 6 to 18 carbon atoms, 0.1% to 15% of a a secondary alcohol of the formula $H(C_2H_4O)_xC_yH_{2y+2}O$ wherein x is 5 to 9 and y is 7 to 11, 0.1% to 10% of a block copolymer of a polyalkylene oxide-modified polydimethyl siloxane and the balance being water.

DETAILED DESCRIPTION OF THE INVENTION

Figure 1:
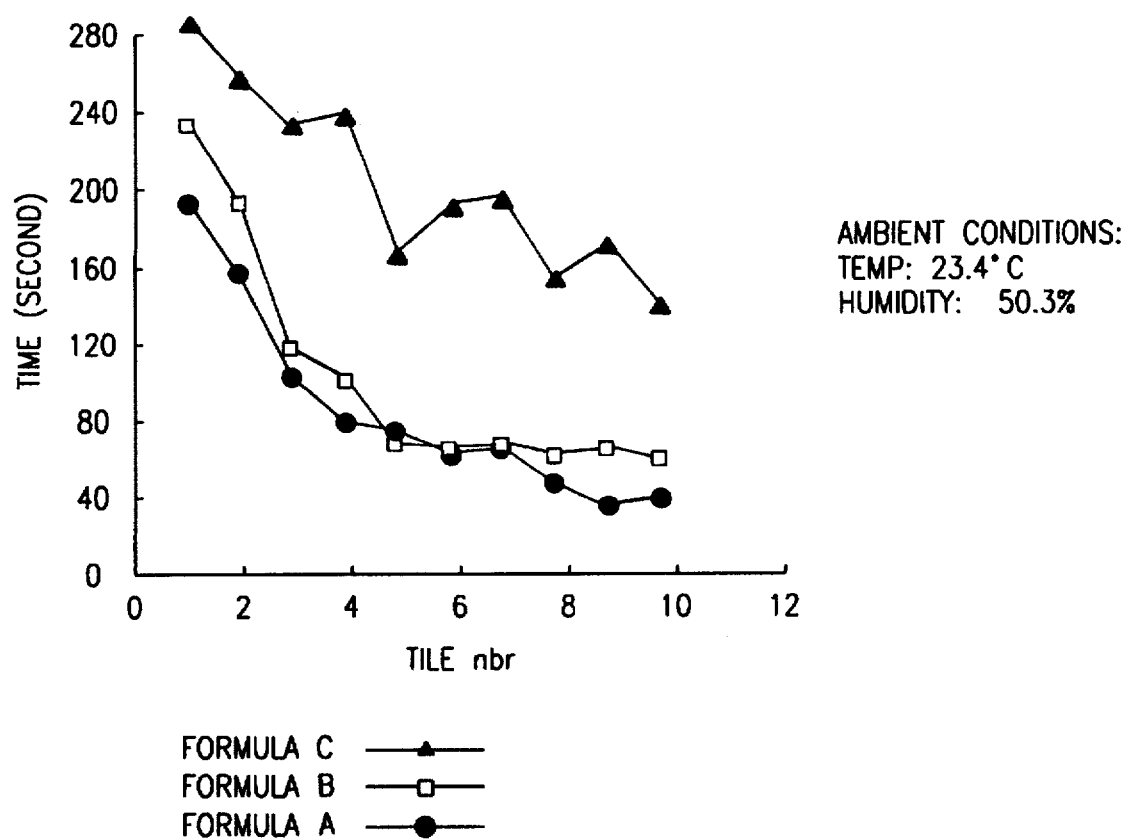
FIG. 1 illustrates a graph of the drying times of Formulas A, B and C.

The present invention relates to a stable optically clear microemulsion composition comprising approximately by weight: 0.1% to 20% of an anionic surfactant, 0.1% to 15% of a a secondary alcohol of the formula $H(C_2H_4O)_xC_yH_{2y+2}O$ wherein x is 5 to 9 and y is 7 to 11, 0.1% to 10% of a block copolymer of a polyalkylene oxide-modified polydimethyl siloxane, 0.1% to 10% of an ethoxylated polyhydric alcohol type compound, 0.4% to 10% of a water insoluble hydrocarbon, essential oil or a perfume and the balance being water.

The present invention also relates to a stable optically clear concentrated microemulsion composition comprising approximately by weight 0.1% to 30% of an anionic surfactant; 0.1% to 10% of an ethoxylated polyhydric alcohol type compound; 0.4% to 10% of a perfume, essential oil or water insoluble hydrocarbon having 6 to 18 carbon atoms; 0.1 to 15% of a secondary alcohol of the formula $H(C_2H_4O)_x C_yH_{2y+2}O$ wherein x is 5 to 9 and y is 7 to 11; 0.1% to 10% of a block copolymer of a polyalkylene oxide-modified polydimethyl siloxane and the balance being water.

The present invention also relates to all purpose hard surface cleaning composition comprising approximately by weight 0.1% to 20% of an anionic surfactant, 0.1% to 10% of a block copolymer of a polyalkylene oxide-modified polydimethyl siloxane, 0 to 15%, more preferably 0.1% to 15% of a secondary alcohol of the formula $H(C_2H_4O)_x C_yH_{2y+2}O$ wherein x is 5 to 9 and y is 7 to 11, 0.1% to 10% of said ethoxylated polyhydric alcohol type compound, 0 to 15% of magnesium sulfate heptahydrate, 0 to 10%, more preferably 0.1 to 10% of a perfume, essential oil or water insoluble hydrocarbon having 6 to 18 carbon atoms and the balance being water.

The present invention also relates to a stable optically clear microemulsion composition comprising approximately by weight: 0.1% to 20% of an anionic surfactant, 0.1% to 15% of a a secondary alcohol of the formula $H(C_2H_4O)_x C_yH_{2y+2}O$ wherein x is 5 to 9 and y is 7 to 11, 0.1% to 10% of a block copolymer of a polyalkylene oxide- modified polydimethyl siloxane, 0.4% to 10% of a water insoluble hydrocarbon, essential oil or a perfume and the balance being water.

The present invention also relates to a stable optically clear concentrated microemulsion composition comprising approximately by weight 0.1% to 30% of an anionic surfactant; 0.4% to 10% of a perfume, essential oil or water insoluble hydrocarbon having 6 to 18 carbon atoms; 0.1 to 15% of a secondary alcohol of the formula $H(C_2H_4O)_x C_yH_{2y+2}O$ wherein x is 5 to 9 and y is 7 to 11; 0.1% to 10% of a copolymer of a polyalkylene oxide-modified polydimethyl siloxane and the balance being water.

The present invention also relates to all purpose hard surface cleaning composition comprising approximately by weight 0.1% to 20% of an anionic surfactant, 0.1% to 10% of a copolymer of a polyalkylene oxide-modified polydimethyl siloxane, 0 to 20%, more preferably 0.1 % to 15% of a secondary alcohol of the formula $H(C_2H_4O)_xC_yH_{2y+2}O$ wherein x is 5 to 9 and y is 7 to 11, 0 to 15% of magnesium sulfate heptahydrate, 0 to 10%, more preferably 0.4 to 10% of a perfume, essential oil or water insoluble hydrocarbon having 6 to 18 carbon atoms and the balance being water.

According to the present invention, the role of the water insoluble hydrocarbon can be provided by a non-water-soluble perfume. Typically, in aqueous based compositions the presence of a solubilizers, such as alkali metal lower alkyl aryl sulfonate hydrotrope, triethanolamine, urea, etc., is required for perfume dissolution, especially at perfume levels of 1% and higher, since perfumes are generally a mixture of fragrant essential oils and aromatic compounds which are generally not water-soluble. Therefore, by incorporating the perfume into the aqueous cleaning composition as the oil (hydrocarbon) phase of the ultimate o/w microemulsion composition, several different important advantages are achieved.

As used herein and in the appended claims the term "perfume" is used in its ordinary sense to refer to and include any non-water soluble fragrant substance or mixture of substances including natural (i.e., obtained by extraction of flower, herb, blossom or plant), artificial (i.e., mixture of natural oils or oil constituents) and synthetically produced substance) odoriferous substances. Typically, perfumes are complex mixtures of blends of various organic compounds such as alcohols, aldehydes, ethers, aromatic compounds and varying amounts of essential oils (e.g., terpenes) such as from 0% to 80%, usually from 10% to 70% by weight, the essential oils themselves being volatile odoriferous compounds and also serving to dissolve the other components of the perfume.

In the present invention the precise composition of the perfume is of no particular consequence to cleaning performance so long as it meets the criteria of water immiscibility and having a pleasing odor. Naturally, of course, especially for cleaning compositions intended for use in the home, the perfume, as well as all other ingredients, should be cosmetically acceptable, i.e., non-toxic, hypoallergenic, etc. The instant compositions show a marked improvement in ecotoxocity as compared to existing commercial products.

The hydrocarbon such as a perfume is present in the dilute o/w microemulsion in an amount of from 0.4% to 10% by weight, preferably from 0.4% to 3.0% by weight, especially preferably from 0.5% to 2.0% by weight, such as weight percent. If the amount of hydrocarbon (perfume) is less than 0.4% by weight it becomes difficult to form the o/w microemulsion. If the hydrocarbon (perfume) is added in amounts more than 10% by weight, the cost is increased without any additional cleaning benefit and, in fact, with some diminishing of cleaning performance insofar as the total amount of greasy or oily soil which can be taken up in the oil phase of the microemulsion will decrease proportionately. In the all purpose hard surface cleaning composition which is not a microemulsion the concentration of the perfume is 0 to 10 wt. %, more preferably 0.1 wt. % to 10wt. %.

In place of the perfume in either the microemulsion composition or the all purpose hard surface cleaning composition at the same previously defined concentrations that the perfume was used in either the microemulsion or the all purpose hard surface cleaning composition one can employ an essential oil or a water insoluble hydrocarbon having 6 to 18 carbon such as a paraffin or isoparaffin.

Suitable essential oils are selected from the group consisting of: Anethole 20/21 natural, Aniseed oil china star, Aniseed oil globe brand, Balsam (Peru), Basil oil (India), Black pepper oil, Black pepper oleoresin 40/20, Bois de Rose (Brazil) FOB, Borneol Flakes (China), Camphor oil, White, Camphor powder synthetic technical, Cananga oil (Java), Cardamom oil, Cassia oil (China), Cedarwood oil (China) BP, Cinnamon bark oil, Cinnamon leaf oil, Citronella oil, Clove bud oil, Clove leaf, Coriander (Russia), Coumarin 69° C. (China), Cyclamen Aldehyde, Diphenyl oxide, Ethyl vanilin, Eucalyptol, Eucalyptus oil, Eucalyptus citriodora, Fennel oil, Geranium oil, Ginger oil, Ginger oleoresin (India), White grapefruit oil, Guaiacwood oil, Gurjun balsam, Heliotropin, Isobornyl acetate, Isolongifolene, Juniper berry oil, L-methyl acetate, Lavender oil, Lemon oil, Lemongrass oil, Lime oil distilled, Litsea Cubeba oil, Longifolene, Menthol crystals, Methyl cedryl ketone, Methyl chavicol, Methyl salicylate, Musk ambrette, Musk ketone, Musk xylol, Nutmeg oil, Orange oil, Patchouli oil, Peppermint oil, Phenyl ethyl alcohol, Pimento berry oil, Pimento leaf oil, Rosalin, Sandalwood oil, Sandenol, Sage oil, Clary sage, Sassafras oil, Spearmint oil, Spike lavender, Tagetes, Tea tree oil, Vanilin, Vetyver oil (Java), Wintergreen The water-soluble organic surfactant materials which are used in forming the ultimate o/w microemulsion compositions of this invention may be selected from the group consisting of water-soluble, non-soap, anionic surfactants mixed with a partially esterified ethoxylated glycerol.

Regarding the anionic surfactant present in the o/w microemulsions any of the conventionally used water-soluble anionic surfactants or mixtures of said anionic surfactants and anionic surfactants can be used in this invention. As used herein the term "anionic surfactant" is intended to refer to the class of anionic and mixed anionic-nonionic detergents providing detersive action.

Suitable water-soluble non-soap, anionic surfactants include those surface-active or detergent compounds which contain an organic hydrophobic group containing generally 8 to 26 carbon atoms and preferably 10 to 18 carbon atoms in their molecular structure and at least one water-solubilizing group selected from the group of sulfonate, sulfate and carboxylate so as to form a water-soluble detergent. Usually, the hydrophobic group will include or comprise a $C_8$–$C_{22}$ alkyl, alkyl or acyl group. Such surfactants are employed in the form of water-soluble salts and the salt-forming cation usually is selected from the group consisting of sodium, potassium, ammonium, magnesium and mono-, di- or tri-$C_2$–$C_3$ alkanolammonium, with the sodium, magnesium and ammonium cations again being preferred.

Examples of suitable sulfonated anionic surfactants are the well known higher alkyl mononuclear aromatic sulfonates such as the higher alkyl benzene sulfonates containing from 10 to 16 carbon atoms in the higher alkyl group in a straight or branched chain, $C_8$–$C_{15}$ alkyl toluene sulfonates and $C_8$–$C_{15}$ alkyl phenol sulfonates.

One preferred sulfonate surfactant is a linear alkyl benzene sulfonate having a high content of 3-(or higher) phenyl isomers and a correspondingly low content (well below 50%) of 2-(or lower) phenyl isomers, that is, wherein the benzene ring is preferably attached in large part at the 3 or higher (for example, 4, 5, 6 or 7) position of the alkyl group and the content of the isomers in which the benzene ring is attached in the 2 or 1 position is correspondingly low. Particularly preferred materials are set forth in U.S. Pat. No. 3,320,174.

Other suitable anionic surfactants are the olefin sulfonates, including long-chain alkene sulfonates, long-chain hydroxyalkane sulfonates or mixtures of alkene sulfonates and hydroxyalkane sulfonates. These olefin sulfonate detergents may be prepared in a known manner by the reaction of sulfur trioxide ($SO_3$) with long-chain olefins containing 8 to 25, preferably 12 to 21 carbon atoms and having the formula $RCH=CHR_1$ where R is a higher alkyl group of 6 to 23 carbons and $R_1$ is an alkyl group of 1 to 17 carbons or hydrogen to form a mixture of sultones and alkene sulfonic acids which is then treated to convert the sultones to sulfonates. Preferred olefin sulfonates contain from 14 to 16 carbon atoms in the R alkyl group and are obtained by sulfonating an a-olefin.

Other example of operative anionic surfactants includes sodium dioctyl sulfosuccinate [di-(2 ethylhexyl) sodium sulfosuccinate being one] and corresponding dihexyl and dioctyl esters. The preferred sulfosuccinic acid ester salts are esters of aliphitic alcohols such as saturated alkanols of 4 to 12 carbon atoms and are normally diesters of such alkanols. More preferably such are alkali metal salts of the diesters of alcohols of 6 to 10 carbons atoms and more preferably the diesters will be from octanol, such as 2-ethyl hexanol, and the sulfonic acid salt will be the sodium salt.

Especially preferred anionic sulfonate surfactants are paraffin sulfonates containing 10 to 20, preferably 13 to 17, carbon atoms. Primary paraffin sulfonates are made by reacting long-chain alpha olefins and bisulfites and paraffin sulfonates having the sulfonate group distributed along the paraffin chain are shown in U.S. Pat. Nos. 2,503,280; 2,507,088; 3,260,744; 3,372,188; and German Patent 735,096.

Examples of satisfactory anionic sulfate surfactants are the $C_8$–$C_{18}$ alkyl sulfate salts and the $C_8$–$C_{18}$ alkyl sulfate salts and the $C_8$–$C_{18}$ alkyl ether polyethenoxy sulfate salts having the formula $R(OC_2H_4)_nOSO_3M$ wherein n is 1 to 12, preferably 1 to 5, and M is a solubilizing cation selected from the group consisting of sodium, potassium, ammonium, magnesium and mono-, di- and triethanol ammonium ions. The alkyl sulfates may be obtained by sulfating the alcohols obtained by reducing glycerides of coconut oil or tallow or mixtures thereof and neutralizing the resultant product.

On the other hand, the alkyl ether polyethenoxy sulfates are obtained by sulfating the condensation product of ethylene oxide with a $C_8$–$C_{18}$ alkanol and neutralizing the resultant product. The alkyl ether polyethenoxy sulfates differ from one another in the number of moles of ethylene oxide reacted with one mole of alkanol. Preferred alkyl sulfates and preferred alkyl ether polyethenoxy sulfates contain 10 to 16 carbon atoms in the alkyl group.

The $C_8$–$C_{12}$ alkylphenyl ether polyethenoxy sulfates containing from 2 to 6 moles of ethylene oxide in the molecule also are suitable for use in the inventive compositions. These surfactants can be prepared by reacting an alkyl phenol with 2 to 6 moles of ethylene oxide and sulfating and neutralizing the resultant ethoxylated alkylphenol.

Other suitable anionic detergents are the $C_9$–$C_{15}$ alkyl ether polyethenoxyl carboxylates having the structural formula $R(OC_2H_4)_nOX$ COOH wherein n is a number from 4 to 12, preferably 5 to 10 and X is selected from the group consisting of $CH_2$, $C(O)R_1$ and

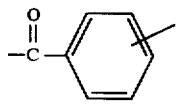

wherein $R_1$ is a $C_1$–$C_3$ alkylene group. Preferred compounds include $C_9$–$C_{11}$ alkyl ether polyethenoxy (7–9) C(O) $CH_2CH_2COOH$, $C_{13}$–$C_{15}$ alkyl ether polyethenoxy (7–9)

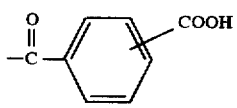

and $C_{10}$–$C_{12}$ alkyl ether polyethenoxy (5–7) $CH_2COOH$. These compounds may be prepared by condensing ethylene oxide with appropriate alkanol and reacting this reaction product with chloracetic acid to make the ether carboxylic acids as shown in U.S. Pat. No. 3,741,911 or with succinic anhydride or phtalic anhydride.

Obviously, these anionic detergents will be present either in acid form or salt form depending upon the pH of the final composition, with the salt forming cation being the same as for the other anionic detergents.

Of the foregoing non-soap anionic sulfonate surfactants, the preferred surfactants are the magnesium salt of the $C_{13}$–$C_{17}$ paraffin or alkane sulfonates.

Generally, the proportion of the nonsoap-anionic surfactant will be in the range of 0.1% to 20.0%, preferably from 1% to 7%, by weight of the dilute o/w microemulsion composition or the all purpose hard surface cleaning composition.

The instant composition can contain a composition (herein after referred to as an ethoxylated polyhydric alcohol type compound such as an ethoxylated glycerol type compound) which is a mixture of a fully esterified ethoxylated polyhydric alcohol, a partially esterified ethoxylated polyhydric alcohol and a nonesterified ethoxylated polyhydric alcohol, wherein the preferred polyhydric alcohol is glycerol, and the compound is

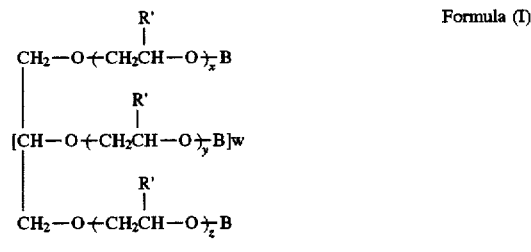

Formula (I)

and

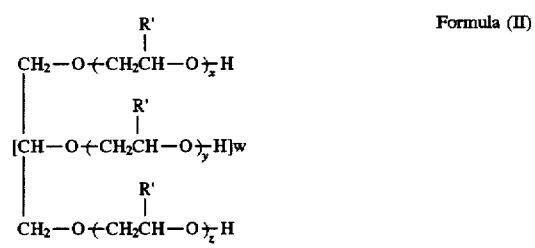

Formula (II)

wherein w equals one to four, most preferably one, and B is selected from the group consisting of hydrogen or a group represented by:

wherein R is selected from the group consisting of alkyl group having 6 to 22 carbon atoms, more preferably 11 to 15 carbon atoms and alkenyl groups having 6 to 22 carbon atoms, more preferably 11 to 15 carbon atoms, wherein a hydrogenated tallow alkyl chain or a coco alkyl chain is most preferred, wherein at least one of the B groups is represented by said

and R' is selected from the group consisting of hydrogen and methyl groups; x, y and z have a value between 0 and 60, more preferably 0 to 40, provided that (x+y+z) equals 2 to 100, preferably 4 to 24 and most preferably 4 to 19, wherein in Formula (I) the weight ratio of monoester/diester/triester is 40 to 90/5 to 35/1 to 20, more preferably 50 to 90/9 to 32/1 to 12, wherein the weight ratio of Formula (I) to Formula (II) is a value between 3 to 0.02, preferably 3 to 0.1, most preferably 1.5 to 0.2, wherein it is most preferred that there is more of Formula (II) than Formula (I) in the mixture that forms the compound.

The ethoxylated glycerol type compound used in the instant composition is manufactured by the Kao Corporation and sold under the trade name Levenol such as Levenol F-200 which has an average EO of 6 and a molar ratio of coco fatty acid to glycerol of 0.55 or Levenol V501/2 which has an average EO of 17 and a molar ratio of tallow fatty acid to glycerol of 1.0. It is preferred that the molar ratio of the fatty acid to glycerol is less than 1.7, more preferably less than 1.5 and most preferably less than 1.0. The ethoxylated glycerol type compound has a molecular weight of 400 to 1600, and a pH (50 grams/liter of water) of 5–7. The Levenol compounds are substantially non irritant to human skin and have a primary biodegradabillity higher than 90% as measured by the Wickbold method Bias-7d.

Two examples of the Levenol compounds are Levenol V-501/2 which has 17 ethoxylated groups and is derived from tallow fatty acid with a fatty acid to glycerol ratio of 1.0 and a molecular weight of 1465 and Levenol F-200 has 6 ethoxylated groups and is derived from coco fatty acid with a fatty acid to glycerol ratio of 0.55. Both Levenol F-200 and Levenol V-501/2 are composed of a mixture of Formula (I) and Formula (II). The Levenol compounds has ecoxicity values of algae growth inhibition >100 mg/liter; acute toxicity for Daphniae>100 mg/liter and acute fish toxicity>100 mg/liter. The Levenol compounds have a ready biodegradability higher than 60% which is the minimum required value according to OECD 301 B measurement to be acceptably biodegradable.

Polyesterified nonionic compounds also useful in the instant compositions are Crovol PK-40 and Crovol PK-70 manufactured by Croda GMBH of the Netherlands. Crovol PK-40 is a polyoxyethylene (12) Palm Kernel Glyceride which has 12 EO groups. Crovol PK-70 which is preferred is a polyoxyethylene (45) Palm Kernel Glyceride have 45 EO groups.

The block of copolymers of polyalkylene oxide-modified polydimethyl siloxane used in the instant compositions at a concentration of about 0.1 to 10.0 wt. %, more preferably 0.25 to 7 wt. % are characterized by the formula:

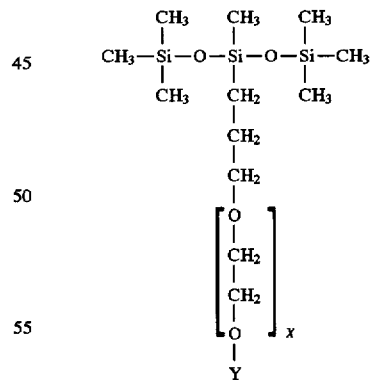

wherein X is from 5 to 18, more preferably 7 to 14 such that the polymer has a molecular weight of about 500 to about 1100, wherein Y is hydrogen or a methyl group. Particularly suitable block copolymers of polyalkylene oxide-modified polydimethyl siloxane are Silwet L-77, Silwet 7607 and Silwet 7608 manufactured by OSI Specialties, Inc. of Danbury, Conn.

The secondary alcohol of the formula $H(C_2H_4O)_xC_yH_{2y+2}O$ wherein x is 5 to 9 and y is 7 to 11 functions as a cosurfactant. A preferred secondary alcohol cosurfactant is DMH-7 manufactured by Union Carbide which is Solvactant™ Solvent DMH-7 having the formula H(CH$_2$CH$_2$O)$_7$ C$_8$H$_{18}$O.

The amount of cosurfactant required to stabilize the microemulsion compositions will, of course, depend on such factors as the surface tension characteristics of the cosurfactant, the type and amounts of the primary surfactants and perfumes, and the type and amounts of any other additional ingredients which may be present in the composition and which have an influence on the thermodynamic factors enumerated above. Generally, amounts of the secondary alcohol cosurfactant used in the microemulsion is in the range of from 0.1% to 15%, preferably from 0.5% to 12%, by weight provide stable dilute o/w microemulsions for the above-described levels of primary surfactants and perfume and any other additional ingredients as described below. The amount of the secondary alcohol cosurfactant in the all purpose hard surface cleaning composition will be in the range of 0.1 to 15%, more preferably 0.5% to 12% by weight.

The ability to formulate neutral and acidic products without builders which have grease removal capacities is a feature of the present invention because the prior art o/w microemulsion formulations most usually are highly alkaline or highly built or both.

The final essential ingredient in the inventive microemulsion compositions having improved interfacial tension properties is water. The proportion of water in the microemulsion or all purpose hard surface cleaning composition compositions generally is in the range of 20% to 97%, preferably 70% to 97% by weight.

As believed to have been made clear from the foregoing description, the dilute o/w microemulsion liquid all-purpose cleaning compositions of this invention are especially effective when used as is, that is, without further dilution in water, since the properties of the composition as an o/w microemulsion are best manifested in the neat (undiluted) form. However, at the same time it should be understood that depending on the levels of surfactants, cosurfactants, perfume and other ingredients, some degree of dilution without disrupting the microemulsion, per se, is possible. For example, at the preferred low levels of active surfactant compounds (i.e., primary anionic and nonionic detergents) dilutions up to 50% will generally be well tolerated without causing phase separation, that is, the microemulsion state will be maintained.

In addition to the above-described essential ingredients required for the formation of the microemulsion composition, the compositions of this invention may often and preferably do contain one or more additional ingredients which serve to improve overall product performance.

One such ingredient is an inorganic or organic salt of oxide of a multivalent metal cation, particularly Mg$^{++}$. The metal salt or oxide provides several benefits including improved cleaning performance in dilute usage, particularly in soft water areas, and minimized amounts of perfume required to obtain the microemulsion state. Magnesium sulfate, either anhydrous or hydrated (e.g., heptahydrate), is especially preferred as the magnesium salt. Good results also have been obtained with magnesium oxide, magnesium chloride, magnesium acetate, magnesium propionate and magnesium hydroxide. These magnesium salts can be used with formulations at neutral or acidic pH since magnesium hydroxide will not precipitate at these pH levels.

Although magnesium is the preferred multivalent metal from which the salts (inclusive of the oxide and hydroxide) are formed, other polyvalent metal ions also can be used provided that their salts are nontoxic and are soluble in the aqueous phase of the system at the desired pH level.

Thus, depending on such factors as the pH of the system, the nature of the primary surfactants and cosurfactant, and so on, as well as the availability and cost factors, other suitable polyvalent metal ions include aluminum, copper, nickel, iron, calcium, etc. It should be noted, for example, that with the preferred paraffin sulfonate anionic detergent calcium salts will precipitate and should not be used. It has also been found that the aluminum salts work best at pH below 5 or when a low level, for example 1 weight percent, of citric acid is added to the composition which is designed to have a neutral pH. Alternatively, the aluminum salt can be directly added as the citrate in such case. As the salt, the same general classes of anions as mentioned for the magnesium salts can be used, such as halide (e.g., bromide, chloride), sulfate, nitrate, hydroxide, oxide, acetate, propionate, etc.

Preferably, in the dilute compositions the metal compound is added to the composition in an amount sufficient to provide at least a stoichiometric equivalent between the anionic surfactant and the multivalent metal cation. For example, for each gram-ion of Mg++ there will be 2 gram moles of paraffin sulfonate, alkylbenzene sulfonate, etc., while for each gram-ion of Al$^{3+}$ there will be 3 gram moles of anionic surfactant. Thus, the proportion of the multivalent salt generally will be selected so that one equivalent of compound will neutralize from 0.1 to 1.5 equivalents, preferably 0.9 to 1.4 equivalents, of the acid form of the anionic surfactant. At higher concentrations of anionic surfactant, the amount of multivalent salt will be in range of 0.5 to 1 equivalents per equivalent of anionic surfactant.

The o/w microemulsion compositions will include from 0% to 2.5%, preferably from 0.1% to 2.0% by weight of the composition of a C$_8$–C$_{22}$ fatty acid or fatty acid soap as a foam suppressant.

The addition of fatty acid or fatty acid soap provides an improvement in the rinseability of the composition whether applied in neat or diluted form. Generally, however, it is necessary to increase the level of cosurfactant to maintain product stability when the fatty acid or soap is present. If more than 2.5 wt. % of a fatty acid is used in the instant compositions, the composition will become unstable at low temperatures as well as having an objectionable smell.

As example of the fatty acids which can be used as such or in the form of soap, mention can be made of distilled coconut oil fatty acids, "mixed vegetable" type fatty acids (e.g. high percent of saturated, mono-and/or polyunsaturated C$_{18}$ chains); oleic acid, stearic acid, palmitic acid, eiocosanoic acid, and the like, generally those fatty acids having from 8 to 22 carbon atoms being acceptable.

Other usual foam suppressants which can be used in the instant composition such fatty alcohol, silicone surfactant.

The all-purpose liquid cleaning composition of this invention may, if desired, also contain other components either to provide additional effect or to make the product more attractive to the consumer. The following are mentioned by way of example: Colors or dyes in amounts up to 0.5% by weight; bactericides in amounts up to 1% by weight; preservatives or antioxidizing agents, such as formalin, 5-bromo-5-nitro-dioxan-1,3; 5-chloro-2-methyl-4-isothaliazolin-3-one, 2,6-di-tert.butyl-p-cresol, etc., in amounts up to 2% by weight; and pH adjusting agents, such as sulfuric acid or sodium hydroxide, as needed. Furthermore, if opaque compositions are desired, up to 4% by weight of an opacifier may be added.

In final form, the all-purpose hard surface liquid cleaning compositions and clear microemulsions exhibit stability at reduced and increased temperatures. More specifically, such compositions remain clear and stable in the range of 5° C. to 50° C., especially 10° C. to 43° C. Such compositions exhibit a pH in the acid or neutral range depending on intended end use. The liquids are readily pourable and exhibit a viscosity in the range of 6 to 60 millipascal.second (mPas.) as measured at 25° C. with a Brookfield RVT Viscometer using a #1 spindle rotating at 20 RPM. Preferably, the viscosity is maintained in the range of 10 to 40 mPas.

The compositions are directly ready for use or can be diluted as desired and in either case no or only minimal rinsing is required and substantially no residue or streaks are left behind. Furthermore, because the compositions are free of detergent builders such as alkali metal polyphosphates they are environmentally acceptable and provide a better "shine" on cleaned hard surfaces.

When intended for use in the neat form, the liquid compositions can be packaged under pressure in an aerosol container or in a pump-type sprayer for the so-called spray-and-wipe type of application.

Because the compositions as prepared are aqueous liquid formulations and since no particular mixing is required to form the o/w microemulsion, the compositions are easily prepared simply by combining all the ingredients in a suitable vessel or container. The order of mixing the ingredients is not particularly important and generally the various ingredients can be added sequentially or all at once or in the form of aqueous solutions of each or all of the primary detergents and cosurfactants can be separately prepared and combined with each other and with the perfume. The magnesium salt, or other multivalent metal compound, when present, can be added as an aqueous solution thereof or can be added directly. It is not necessary to use elevated temperatures in the formation step and room temperature is sufficient.

The instant microemulsion formulas explicitly exclude alkali metal silicates and alkali metal builders such as alkali metal polyphosphates, alkali metal carbonates, alkali metal phosphonates and alkali metal citrates because these materials, if used in the instant composition, would cause the composition to have a high pH as well as leaving residue on the surface being cleaned.

It is contemplated within the scope of the instant invention that the instant partially esterified ethoxylated polyhydric alcohol compound can be employed in hard surface cleaning compositions such as wood cleaners, window cleaners and light duty liquid cleaners.

The following examples illustrate liquid cleaning compositions of the described invention. Unless otherwise specified, all percentages are by weight. The exemplified compositions are illustrative only and do not limit the scope of the invention. Unless otherwise specified, the proportions in the examples and elsewhere in the specification are by weight.

Example 1
The following compositions in wt. % were prepared by simple mixing at 25° C.:

|  | A | B | C | D | E |
|---|---|---|---|---|---|
| Sodium $C_{13}$–$C_{17}$ paraffin sulfonate | 4.7 | 4.7 | 4.7 | 4.7 | 4.7 |
| Silwet 7608 | 0.75 | 0.75 | — | 2.3 | 2.3 |
| Levenol F-200 | 2.3 | 2.3 | 2.3 | — | — |
| DMH-7 | 4.0 | — | — | 4.0 | — |
| Coco fatty acid | — | — | 0.75 | — | — |

-continued

Example 1
The following compositions in wt. % were prepared by simple mixing at 25° C.:

|  | A | B | C | D | E |
|---|---|---|---|---|---|
| Nonionic defoamer | — | — | — | 1 | 1 |
| Silicone Antifoam | — | — | — | 0.02 | 0.02 |
| $MgSO_4 \cdot 7H_2O$ | 1.76 | 1.76 | 2.2 | 1.76 | 1.76 |
| Perfume (a) | 0.8 | 0.8 | 0.8 | 0.8 | 0.8 |
| DEGMBE | — | 4.0 | 4 | — | 4.0 |
| Water | Bal. | Bal | Bal | Bal. | Bal |
| pH | 7 | 7 | 7 | 7 | 7 |
| Degreasing test |  |  |  |  |  |
| Neat (b) | 20 | 20 | 20 | 20 | 20 |
| Dilute (b) | 20 | 25 | 45 | 20 | 20 |

(a) contains 25% by weight of terpenes.
(b) the lower the number of strokes, the better the degreasing performance.

DRYING TEST

Figure 2:
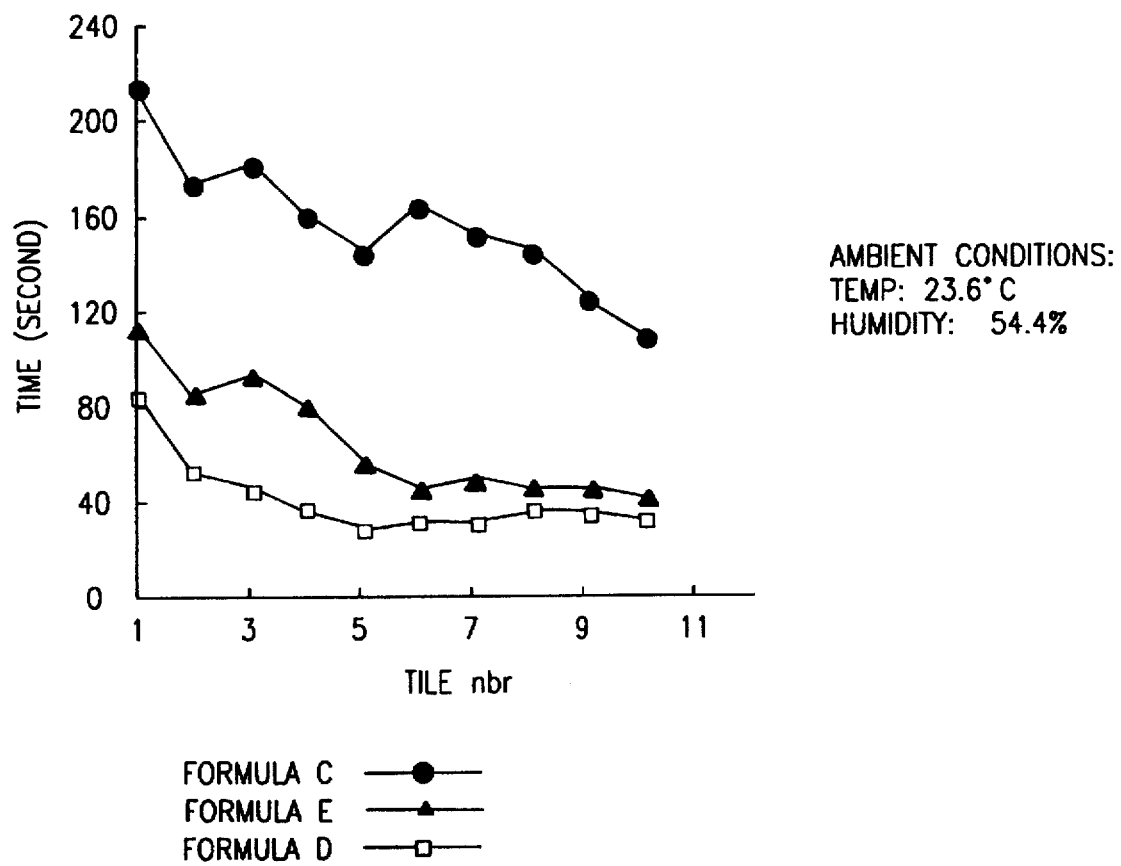
FIG. 2 illustrates a graph of the drying times of Formulas C, D and E.

The instant compositions are tested in dilute condition (recommended dosage-tap water). The selected support is black brilliant PMMA tile used also to visualize residues. A piece of cotton (polyester-cotton) floor-cloth is immersed in the solution of cleaning product (recommended use concentration). The excess of product is squeezed out. The floor-cloth as well as the black brilliant PMMA tile is placed in a machine. The pressure at the interface (cloth/tile) is adjusted at ca. 1 kg. The machine operates for 15 sec. The tiles (5 –15 replicates per product) are dried in open air and the drying time per tile is recorded. The drying time means are reported on the above table. FIG. 1 illustrates the drying times of Formulas A, B and C. FIG. 2 illustrates the drying times of Formulas C, D and E.

In summary, the described invention broadly relates to an improvement in microemulsion and all purpose hard surface cleaning compositions containing an anionic surfactant, a drying agent, a partially esterified ethoxylated polyhydric alcohol, a secondary alcohol cosurfactant, a hydrocarbon ingredient and water.

What is claimed:

1. A composition comprising:

(a) 0.1 wt. % to 10 wt. % of a mixture of

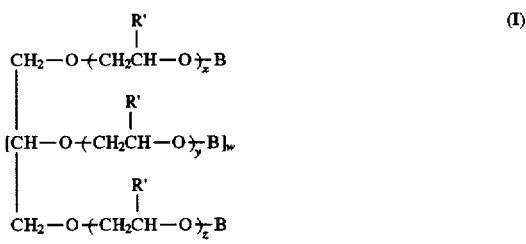

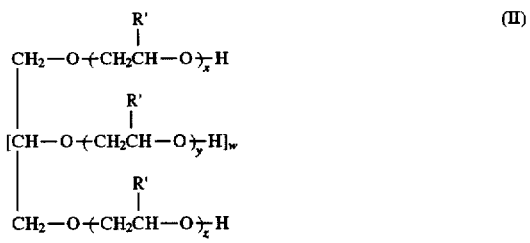

wherein w equals one to four, and B is selected from the group consisting of hydrogen and a group represented by:

wherein R is selected from the group consisting of alkyl group having 6 to 22 carbon atoms, and alkenyl groups having 6 to 22 carbon atoms, wherein at least one of the B groups is represented by said

R' is selected from the group consisting of hydrogen and methyl groups; x, y and z have a value between 0 and 60, provided that (x+y+z) equals 2 to 100, wherein in Formula (I) the weight ratio of monoester/diester/triester is 40 to 90/5 to 35/1 to 20, wherein the weight ratio of Formula (I) and Formula (II) is a value between 3 and 0.02;
- (b) 0.1 to 10 wt. % of a block copolymer of a polyalkylene oxide-modified polydimethyl siloxane;
- (c) 0.1 wt. % to 20 wt. % of an anionic surfactant;
- (d) 0.1 wt. % to 15 wt. % of a secondary alcohol cosurfactant having the formula: $H(C_2H_4O)_xC_yH_{2y+2}O$, wherein x is 5 to 9 and y is 7 to 11;
- (e) 0.1 wt. % to 10 wt. % of a water insoluble hydrocarbon, essential oil or a perfume; and
- (f) the balance being water.

2. The composition of claim 1 which further contains a salt of a multivalent metal cation in an amount sufficient to provide from 0.5 to 1.5 equivalents of said cation per equivalent of said anionic surfactant.

3. The composition of claim 2 wherein the multivalent metal cation is magnesium or aluminum.

4. The composition of claim 3 wherein said salt of said metal cation multivalent is magnesium oxide or magnesium sulfate.

5. The composition of claim 1 further including a fatty acid which has 8 to 22 carbon atoms.

6. The composition of claim 1 wherein the anionic surfactant is a $C_9$–$C_{15}$ benzene sulfonate or a $C_{10}$–$C_{20}$ alkane sulfonate.

7. A microemulsion composition comprising:
- (a) 0.1 to 10 wt. % of a block copolymer of a polyalkylene oxide-modified polydimethyl siloxane;
- (b) 0.1 wt. % to 20 wt. % of an anionic surfactant;
- (c) 0.1 wt. % to 15 wt. % of a secondary alcohol cosurfactant having the formula: $H(C_2H_4O)_xC_yH_{2y+2}O$, wherein x is 5 to 9 and y is 7 to 11;
- (d) 0.4 wt. % to 10 wt. % of a water insoluble hydrocarbon, essential oil or a perfume; and
- (e) the balance being water.

8. The microemulsion composition of claim 7 which further contains a salt of a multivalent metal cation in an amount sufficient to provide from 0.5 to 1.5 equivalents.

9. The microemulsion composition of claim 8 wherein the multivalent metal cation is magnesium or aluminum.

10. The microemulsion composition of claim 7 further including a fatty acid which has 8 to 22 carbon atoms.

11. The microemulsion composition of claim 7 wherein the anionic surfactant is a $C_9$–$C_{15}$ alkyl benzene sulfonate or a $C_{10}$–$C_{20}$ alkane sulfonate.

* * * * *